United States Patent
Conway

(10) Patent No.: US 6,565,804 B1
(45) Date of Patent: May 20, 2003

(54) METHOD OF DISINFECTING AND INHIBITING MOLD AND MILDEW GROWTH ON NON-POROUS HARD SURFACES

(75) Inventor: Mary J. Conway, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/486,936

(22) PCT Filed: Sep. 2, 1998

(86) PCT No.: PCT/US98/18263

§ 371 (c)(1),
(2), (4) Date: Jun. 9, 2000

(87) PCT Pub. No.: WO99/11123

PCT Pub. Date: Mar. 11, 1999

Related U.S. Application Data

(60) Provisional application No. 60/056,279, filed on Sep. 3, 1997.

(51) Int. Cl.⁷ .................................................. A61L 2/18
(52) U.S. Cl. ......................................... 422/28; 424/405
(58) Field of Search ............................. 422/28; 424/405

(56) References Cited

U.S. PATENT DOCUMENTS

| | | |
|---|---|---|
| 3,463,735 A | 8/1969 | Stonebraker et al. |
| 3,836,669 A | 9/1974 | Dadeklan et al. |
| 4,336,151 A | 6/1982 | Like et al. |
| 4,444,790 A | 4/1984 | Green et al. |
| 4,464,398 A | 8/1984 | Sheets et al. |
| 4,540,505 A | 9/1985 | Frazier |
| 5,320,147 A | 6/1994 | Schaeufele |
| 5,591,442 A * | 1/1997 | Diehl et al. .................. 424/401 |

FOREIGN PATENT DOCUMENTS

| | | |
|---|---|---|
| EP | 0 647 706 | 4/1995 |
| GB | 1311534 | 3/1973 |
| GB | 2319179 | 5/1998 |
| JP | 02152916 A * | 6/1990 |
| WO | WO 93/16162 | 8/1993 |
| WO | WO 93/25654 | 12/1993 |
| WO | WO 97/29173 | 8/1997 |

* cited by examiner

Primary Examiner—Elizabeth McKane

(57) ABSTRACT

A method of cleaning, disinfecting, and inhibiting mold and mildew growth on a non-porous hard surface is disclosed. The method utilizes a composition comprising an aliphatic alcohol, at least one organic ether, and optionally a secondary alcohol and is essentially free of conventional antibacterial agents including chlorine bleaches, quaternary ammonium compounds and phenolic compounds.

18 Claims, No Drawings

METHOD OF DISINFECTING AND INHIBITING MOLD AND MILDEW GROWTH ON NON-POROUS HARD SURFACES

PRIORITY

This application claims the benefit of U.S. Provisional Application No. 60/056,279, filed Sep. 3, 1997.

TECHNICAL FIELD

This invention relates to aqueous cleaning, sanitizing, disinfecting and mold and mildew inhibiting compositions for non-porous hard surfaces such as glass (e.g., mirrors and shower doors), glazed porcelain, metallic (e.g., chrome, stainless steel, and aluminum), ceramic tile, enamel, fiberglass, Formica®, Corian® and plastic. The compositions utilize surprisingly low concentrations of particular alcohols as well as advantageously leave very low levels of residue on the surface.

BACKGROUND ART

Complete elimination of pathogenic micro-organisms on various surfaces, especially hard surfaces where such organisms may stay active for relatively long periods of time, has long been a goal of those charged with cleaning and maintaining in an antiseptic fashion kitchens and bathrooms in the home, as well as in commercial and institutional settings such as hospitals, medical clinics, hotels and restaurants. A further goal has been to prevent the formation of allergens caused by the growth of mold and mildew on bathroom surfaces.

A variety of chemical disinfecting agents have been developed to accomplish these goals. However, some of these agents have disadvantages in that some are corrosive, unpleasant to smell or capable of staining certain surfaces that commonly need to be cleaned and disinfected. Additionally, if the agents are volatile organic compounds, the compositions are environmentally disadvantageous when utilized at higher concentrations. Furthermore, some disinfecting agents contain components which leave residual solids on surfaces such as glass, polished tile, or metals which detract from the visual appearance of these surfaces.

Chlorine bleaches such as aqueous sodium hypochlorite have long been recognized as being effective against all types of micro-organisms, provided that the bleach is used in sufficiently high concentrations, such as 5,000 ppm (0.5%) of active sodium hypochlorite and higher, depending on the micro-organism to be eliminated. These types of solutions are recommended for use for disinfecting an area where blood or other potentially pathogenic biological contaminants have been spilled or released and total disinfection is required. At such high levels of sodium hypochlorite, the sensory irritation from the chlorine smell from the bleach simply makes this agent undesirable for routine cleaning and disinfection of, for example, hospital rooms, where patients remain in the room during and after the cleaning and disinfection process.

Disadvantageously, hypochlorites may also stain or degrade some surfaces such as Formica®. Additionally, bleaches demonstrate high reactivity with other cleaning agents. For example, bleach when combined with ammonia produces harmful chloramine gas. Also, bleach when combined with an acid based cleaner produces chlorine gas, which is potentially hazardous.

Consumers are also highly sensitive to streaking and hazing which may develop on windows, shower doors and mirrors, and the like. A desirable cleaner should produce a surface which exhibits little or no change in clarity and optical properties from the moment of use and ideally remain that way for weeks and months. In the context of the present invention, streaking can be defined as a visible diffractive layer which causes light scattering. Hazing can be described as a misty diffractive layer that covers the entire surface developing instantly or over time, which clouds the surface. Most cleaning products leave behind a thin residual film of product in intimate contact with the surface. Hydrogen bonding to the surface oxides and/or hydroxides with continuous attachment produces an optically clear film. Small breaks or disruptions in these continuous residual films cause diffractive streaks which are visible to the naked eye. Similarly, residual diffractive particles will also be visible to the naked eye. Specific formulation techniques are required to maintain the integrity of a homogeneous residual film and to eliminate residual diffractive particles on the cleaned surface.

Chemical and optical stability of the residual surface film may be achieved by maintaining a proper balance of surfactants and coupling agents in the formula. More typically, however, the formulator will prepare a cleaning composition to ensure stability of the composition and the delivery of good disinfecting properties without considering the residual film properties and optical effects. For example, Quaternary ammonium compounds have long been recognized as being useful for their antibacterial properties, as can be seen from U.S. Pat. No. 3,836,669 to Dadekian; U.S. Pat. No. 4,320,147 to Schaeufele; U.S. Pat. No. 4,336,151 to Like et al.; U.S. Pat. No. 4,444,790 to Green et al.; U.S. Pat. No. 4,464,398 to Sheets et al.; and U.S. Pat. No. 4,540,505 to Frazier. However, quaternary ammonium compounds have a tendency to contribute to visible streaking on glass and other surfaces.

An additional disadvantage of quaternary ammonium based compositions is that the addition of common highly efficacious cleaning surfactants such as anionic surfactants is not possible due to incompatibility. Accordingly, more costly surfactants must be employed in quaternary ammonium formulations.

Further, quaternary ammonium compounds are known eye and skin irritants, thus special care must be taken by the user of compositions employing these compounds.

To minimize expense, undesirable odors and possible detrimental effects of disinfecting agents on surfaces to be disinfected, it is desirable to minimize the amount of disinfecting or mold and mildew inhibiting agents used while still retaining efficacy. As will be explained in greater detail below, it has been found that a combination of specific alcohols, and glycol ethers at a pH in the range of from about 4.0 to about 13.0 provides a composition that is effective as a cleaner, disinfectant and a mold and mildew prevention agent on non-porous hard surfaces.

DISCLOSURE OF INVENTION

One object of this invention is to provide compositions that can be used in a method of cleaning and disinfecting various surfaces. Another object of this invention is to provide such compositions that inhibit mold and mildew growth on surfaces.

A particularly advantageous object of this invention is to provide compositions that can be used in household, commercial and institutional settings for cleaning and disinfection purposes that are more tolerable to people remaining in the area disinfected because the smell of the compositions is more appealing to the user than if highly concentrated hypochlorite bleach compositions were used as the active disinfectant. Yet another object is to provide cleaning, disinfecting and mold and mildew inhibiting compositions that do not have high concentrations of certain compounds which are prone to corrode or stain surfaces to be treated.

Further, it is an object of this invention to provide disinfectancy and mold and mildew inhibition on surfaces at reduced levels of environmentally disadvantageous volatile organic compounds.

Another object of the invention is to provide a method of using the composition as a rinsing aid to maintain a clean and disinfected shower and prevent the build-up of undesirable deposits on shower surfaces.

Additionally, it is an object of the present invention to reduce the potential of disinfecting compositions to cause visible streaks on glass and polished surfaces when compared to disinfectants containing quaternary ammonium compounds.

These and other objects of the present invention are provided by applying to a non-porous hard surface, an effective amount of an aqueous cleaning composition comprising an aliphatic alcohol, a glycol ether or ethers, and optionally, a secondary alcohol selected from the group consisting of monohydric alcohols, dihydric alcohols, trihydric alcohols and polyhydric alcohols, at a pH in the range of from about 4.0 to about 13.0. The composition may also contain other conventional materials including, but certainly not limited to; surfactants, chelating agents, pH modifiers, hydrotropes, fragrances, dyes, etc. Surprisingly, these compositions provide cleaning, disinfectancy and mold and mildew inhibiting properties at significantly reduced levels of volatile organic compounds without the need for chlorine bleaches, quaternary ammonium or phenolic compounds.

The first component of the present invention is an aliphatic alcohol. Exemplary aliphatic alcohols include isopropanol, propanol, butanol and ethanol. The preferred aliphatic alcohol is isopropanol, due to its evaporation and low odor characteristics. Methyl alcohol, however, is less favored due to its toxicity.

Typically the aliphatic alcohol is utilized in an amount of up to about 10%; preferably from about 1.0% to about 10.0%; and most preferably from about 3.5% to about 10.0% by weight of the composition (hereinafter, all amounts are given in weight percent, unless specified otherwise).

A further component of the present invention is an organic ether. The organic ethers according to the present invention are represented by the following Formula (I):

$$R_1-O-R_2 \quad (I)$$

wherein $R_1$ is a $C_1-C_8$ linear, branched, or cyclic alkyl or alkenyl optionally substituted with —OH, —OCH$_3$, or —OCH$_2$CH$_3$, and $R_2$ is a $C_1-C_6$ linear, branched or cyclic alkyl or alkenyl substituted with —OH.

Preferably, $R_1$ is an optionally substituted $C_3-C_6$ alkyl or alkenyl, and $R_2$ is a monosubstituted $C_2-C_4$ linear or branched alkyl or alkenyl.

More preferably, $R_1$ is an unsubstituted or monosubstituted linear or branched $C_3-C_6$ alkyl, and $R_2$ is a monosubstituted $C_2-C_4$ linear or branched alkyl.

Most preferably, $R_1$ is an unsubstituted n-$C_3$–$C_4$ or n-$C_6$ linear alkyl or

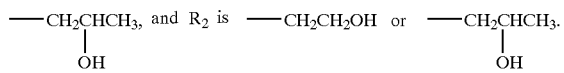

The preferred organic ethers are the glycol ethers. Suitable glycol ethers include ethylene glycol n-hexyl ether, (available as Hexyl Cellosolve®, from Union Carbide Corporation), ethylene glycol mono-butyl ether (available as Butyl Cellosolve®, from Union Carbide Corporation, or as Dowanol® EB, from Dow Chemical Co.), dipropylene glycol methyl ether (available as Dowanol® DPM, from Dow Chemical Co.), propylene glycol n-butyl ether (sold as Dowanol® PnB), propylene glycol tertiary-butyl ether (available as Arcosolv® PTB from Arco Chemicals), and propylene glycol n-propyl ether (available as Dowanol® PnP from Dow Chemical Co.). Other useful glycol ethers include other P-series glycol ethers such as propylene glycol methyl ether (sold as Dowanol® PM), dipropylene glycol n-Butyl Ether (sold as Dowanol® DPnB), and dipropylene glycol n-Propyl Ether (sold as Dowanol® DPnP) and mixtures thereof.

In the present invention, the glycol ether(s) are generally present in the range from about 0.01 to about 10.0 total weight percent. Preferably, the glycol ether component is employed in the range from about 0.5% to about 10.0%; and most preferably, from about 0.9% to about 8.0% by weight of the composition, depending upon the specific glycol ether.

Ideally the glycol ether component is a mixture of ethers, each present in a range of from about 0.01% to about 10%. Preferably the composition comprises 1.2% or less by weight of ethylene glycol n-hexyl ether and from about 0.01% to about 10.0%, more preferably from about 0.01% to about 3.0% by weight of ethylene glycol n-butyl ether. With respect to the Hexyl, it has been found beneficial to use this component at or near its solubility limit of 1.0% in an aqueous solution.

It has been found that certain alcohols couple with the nonvolatile organic ethers above, and markedly reduce the potential for the formation of visible streaks. These secondary alcohols include various monohydric alcohols, dihydric alcohols, trihydric alcohols, and polyhydric alcohols. Suitable secondary alcohols for use in the present invention are represented by the following Formula (II):

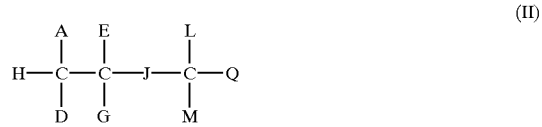

wherein A, D, E, G, L and M are independently —H, —CH$_3$, —OH or —CH$_2$OH; J is a single bond or —O—; and Q is —H or a straight chain $C_1-C_5$ alkyl optionally substituted with —OH, with the proviso that:

(i) if Q is not an alkyl substituted with —OH, then at least one of A, D, E, G, L and M is —OH or —CH$_2$OH;

(ii) when only one of A and E is —OH and J is a single bond, D, G, L, M and Q may not be —H simultaneously;

(iii) when A, D, E, G and L are —H simultaneously, J is a single bond and M is

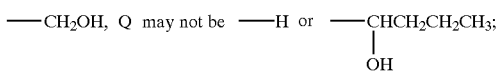

and (iv) when J is single bond, none of E, G, L and M is —CH$_3$ or —CH$_2$OH and Q is —CH$_2$CH$_2$CH$_2$CH$_3$, then at least two of A, D, E, G, L and M are —OH; or at least one of A and D is —CH or —CH$_2$OH.

Preferably, at least one of A, D, E and G is —OH or —CH$_2$OH and Q is —H or a straight chain C$_1$-C$_5$ alkyl optionally monosubstituted with —OH.

More preferably, one or two of A, D, E and G is —OH or —CH$_2$OH and Q is —H or —CH$_2$OH.

Most preferably, one or two of A, D, E and G is —OH or —CH$_2$OH, J is —O—, L and M are independently —H or —CH$_3$ and Q is —CH$_2$OH. The most preferred secondary alcohol has been found to be propylene glycol.

In the present invention, the secondary alcohol will be generally employed in the range of up to about 5.0%; preferably from about 0.1% to about 3.5%; and most preferably, from about 0.2% to about 2.5% by weight of the composition.

Compositions of the present invention typically have a pH of about 4 or above, more preferably from about 7 to about 13 and ideally from about 9.5 to about 12.5. The pH may be adjusted by conventional pH adjusting agents such as citric acid, acetic acid, sodium hydroxide, potassium hydroxide, ammonia and mixtures thereof.

The compositions utilized in the present invention are typically water-based for reasons of household safety and commercial acceptance. Soft, distilled or deionized water are preferred as the source of water for dilution of the individual components as well as for the water added as the balance of the composition for such use as an aqueous shower rinsing solution.

Generally, the amount of water utilized is dependent on the particular application of the composition. For household disinfecting compositions, water is typically present in an amount from about 1.0% to about 95%; preferably 50% to about 95%; and most preferably from about 85% to about 95% by weight of the composition.

Builder salts and chelating agents of the type conventionally used in liquid detergent compositions for cleaning hard surfaces may also be included in the compositions of the present invention in small amounts, generally less than about 5%, provided that they do not promote streaking on surfaces. Such builder salts include sodium sesquicarbonate, sodium carbonate, sodium gluconate, sodium citrate, sodium borate, potassium carbonate, tetrapotassium pyrophosphate, sodium metasilicate and the like, and such polymeric materials as polyacrylic acid. The chelating agents may include water soluble chelating agents such as alkali metal or substituted ammonium amino polycarboxylates such as sodium or potassium salts of ethylenediamine tetraacetic acid ("EDTA") such as tetrasodium EDTA.

The compositions according to the present invention may contain one or more surfactants to adjust the surface tension of the composition and to aid in cleaning. These surfactants may include anionic surfactants such as sodium dodecyl benzene sulfonate, decyl(sulfophenoxy)benzenesulfonic acid disodium salt sold by Dow Corp. as Dowfax® C10L, and sodium lauryl sulfate, or amphoteric surfactants such as caprylic glycinate sold by Witco Corp. as Rewoteric® AMV.

The anionic surfactant may also be a fluoro anionic surfactant such as 3M Fluorad® FC-129. Other suitable surfactants include betaine surfactants such as coco amido propyl dimethyl sultaine sold by Lonza Corp. as Lonzaine® CS, coconut based alkanolamide surfactants sold by Mona Chemicals as Monamid® 150-ADD or nonionic surfactants including the ethoxylated alcohols such as Neodol® 23-3 and Neodol® 23-5(Shell Chemicals), alkyl phenol ethoxylates, and Igepal CO-630 (Rhone-Poulenc); low foaming surfactants such as lauramine oxide sold by Lonza Corp. as Barlox® LF and cleaning surfactants such as ethoxylated vegetable oil sold by GAF Corp. as Emulphor® EL-719.

It is believed that the use of cationic amphoteric surfactants may result in cleaners which have a tendency for streaking or smearing problems. Accordingly, amphoteric surfactants used in the present invention are preferably employed under alkaline conditions to render the anionic portion of the amphoteric compound active.

Ideally, the amphoteric surfactant exhibits high detergency and low foam characteristics. Suitable examples of such amphoteric compounds include a capryloamphodipropionate such as Amphoterge® KJ-2 (Lonza Corp.) which has a lipophilic end with a chain length including the amide carbon of C$_6$ (4%); C$_8$ (57%); C$_{10}$ (38%) and C$_{12}$ (1%).

The amphoteric surfactants may desirably be utilized in their salt-free forms to maximize their compatibility in the cleaning systems, particularly if the cleaner contains detergents.

In the present invention, the surfactant(s) will be employed in the range from 0 to about 5.0%; preferably in the range of from about 0.01% to about 3.0%; and most preferably in the range of from about 0.01% to about 2.0% by weight of the composition.

The formulator may also choose to include one or more cleaning solvents or cleaning supplements such as monoethanolamine. These cleaning solvents will typically be utilized in amounts from 0 to about 2.0%, preferably from about 0.01% to about 1.0% and most preferably, from about 0.125% to about 0.8% by weight of the composition.

Thickening agents may also be utilized where there is a need to increase the time the consumer can wipe the composition before it runs down a vertical surface. Suitable thickening agents include polyacrylic acid polymers and copolymers such as Carbopol® ETD 2623 (B. F. Goodrich Co.) or Accusol 821 (Rohm and Haas).

For better consumer acceptance, the glass cleaning composition will typically contain colorant or dye, such as Direct Blue 86, or polymeric colorants such as Liquitint® Blue HP and a fragrance component. If a dye or a fragrance is contained in the composition, it may be preferable also to include an anti-oxidant, such as potassium iodide, to protect these materials and provide sufficient stability for a long shelf life. If the fragrance oil utilized which is not already preblended with a solubilizer, a fragrance solubilizer, such as Igepal-CO 630 commercially available from Rhone-Poulenc, or an alkoxylated linear alcohol such as PolyTergent SL-62 from Olin Chemical, is preferably utilized in a 50:50 blend with the fragrance. Of course, it is certainly possible for commercial or other reasons to provide a clear or fragrance-free composition by omitting these materials.

MODES OF CARRYING OUT THE INVENTION

The following Examples are provided to show various aspects of the present invention without departing from the scope and spirit of the invention. Unless otherwise indicated, all parts and percentages used in the following Examples are by weight.

Generally, the compositions can be prepared by blending the ingredients in any order. It is preferred that if the fragrance does not contain a solubilizer, a 50:50 preblend of these components is added to the composition. It is also desirable to prepare the compositions of the present invention by first admixing the surfactant component (if utilized), water and at least a portion of the alcohols before incorporating the glycol ether(s). Preferably the components are admixed with stirring to hasten dissolution. Mixing is done at ambient temperature.

The following ingredients were used in the compositions described in the Examples:

Ammonium Hydroxide (28%)—ammonium hydroxide solution at 28% ammonia concentration.

Caustic Soda (50%)—aqueous solution of sodium hydroxide at 50% active concentration.

Sodium Docecyl Benzene Sulfonate (36%)—aqueous solution of sodium docecyl benzene sulfonate at 36% active concentration.

EXAMPLE 1

An aqueous antibacterial composition according to the present invention was prepared according to the following formula:

| | |
|---|---|
| Sodium dodecyl benzene sulfonate | 0.2000 |
| Isopropanol, anhydrous | 3.5000 |
| Ethylene glycol n-hexyl ether | 0.9000 |
| Ethylene glycol mono-butyl ether | 1.0000 |
| Ammonium hydroxide | 0.3000 |
| Propylene glycol | 0.2500 |
| Fluorad ® FC-129 fluoro surfactant | 0.0200 |
| Fragrance with solubilizer (50:50 blend) | 0.0500 |
| Caustic soda | 0.0600 |
| Soft Water | balance |

This formula has a pH in the range of about 11.5 to about 12.2. When tested for use as an antibacterial composition, all tested slides/carriers of staphylococcus aureus showed no indication of bacterial growth after treatment. This composition was also tested using deionized water rather than soft water, and found to be equally effective. When reformulated to eliminate the ammonium hydroxide, no loss of effectiveness was noted.

EXAMPLE 2

An aqueous shower rinsing composition according to the present invention was prepared according to the following formula:

| | |
|---|---|
| Sodium dodecyl benzene sulfonate | 0.2000 |
| Isopropanol, anhydrous | 3.5000 |
| Ethylene glycol n-hexyl ether | 0.9000 |
| Ethylene glycol mono-butyl ether | 1.0000 |
| Igepal ® CO-630, fragrance solubilizer | 0.0250 |
| Propylene glycol | 0.2500 |
| Fluorad ® FC-129 fluoro surfactant | 0.0200 |
| Fragrance | 0.0250 |
| Caustic soda, 50% active | 0.0600 |
| Deionized Water | balance |

This formula has a pH in the range of about 11.5 to about 12.2.

Comparative Example 2A

A commercially available cleaning product sold under the tradename Clean Shower was analyzed and is believed to have the following composition:

| | |
|---|---|
| Ethoxylated Fatty ester (surfactant) | 0.7000 |
| Ethylenediaminetetracetic Acid salts | 1.2000 |
| Isopropyl alcohol | 2.4000 |
| Fragrance | Present |
| Ammonia | Present |
| Water | balance |

The pH of this product was measured as 4.9.

Comparative Example 2B

A commercially available cleaning product sold under the tradename Tilex Fresh Shower was analyzed and is believed to have the following composition:

| | |
|---|---|
| Ethoxylated Fatty ester (surfactant) | 1.80 |
| Ethylenediaminetetracetic Acid salts | 1.10 |
| Isopropyl alcohol | 2.20 |
| Fragrance | Present |
| Ammonia | Present |
| Water | balance |
| The pH of this product was measured as 11.4. | |

The aqueous shower rinsing compositions of Examples 2, 2A and 2B are applied onto shower surfaces after showering to prevent the build-up of deposits such as soap scum, minerals, germs, bacteria, mold and mildew. These examples were also tested for antibacterial effect, as in Example 1. Of these Examples, Example 2 passed this test, while Examples 2A and 2B failed in terms of antibacterial efficacy.

In addition to the above comparative Examples, additional tests were conducted to evaluate the effectiveness of several shower rinsing compositions for ability to reduce soap scum residue. A standard soap scum solution was prepared by weighing a specified amount of Racine Wisconsin tap water (approximately 125 ppm calcium carbonate) into a large beaker. The water was heated to 160° F., and specified amounts of bath soap, shampoo plus conditioner, shave gel, synthetic sebum, Bandy Black clay were added. The solution was mixed well for ten minutes, then cooled to 120° F. before application to tile test surfaces. Four tile by three tile black ceramic tile boards were used as test surfaces. Glossmeter readings were taken on clean tiles before treatment, using a conventional gloss meter. To simulate a shower, four sprays of room temperature tap water were sprayed on the tile surface. After waiting one minute, four sprays of soap scum solution were applied evenly to the tile test surface. After one minute, four strokes of comparative example formulation were evenly applied and allowed to air dry. After the tile surfaces had dried, this was considered to be one application. For purposes of the test, a total of seven applications were made. Gloss meter readings were taken of the tiles after seven application, and the change in gloss (gloss of clean tiles minus the gloss of the test tiles after seven applications) was calculated. The compositions tested are as follows.

TABLE 1

| Raw Material | Example 1 | Example 2C | Example 2D | Example 2E | Example 2F | Example 2G |
|---|---|---|---|---|---|---|
| Deionized Water | | 92.23 | 93.87 | 93.86 | 92.34 | 94.13 |
| Monoethanolamine | | 0.20 | | | | |
| Acusol 445N | | | | 0.02 | | |
| Acusol 820 | | | | | 0.03 | |
| Soft Water | 93.72 | 0.00 | 0.00 | 0.00 | 0.00 | 0.00 |
| SDBS | 0.20 | 0.40 | 0.40 | 0.40 | 0.40 | 0.20 |
| Fluorad FC-129 | 0.02 | 0.02 | 0.02 | 0.02 | 0.02 | 0.02 |
| Hexyl Cellosolve | 0.90 | 1.20 | 1.20 | 1.20 | 1.20 | 0.90 |
| Butyl Cellosolve | 1.00 | 3.00 | 2.00 | 2.00 | 3.00 | 1.00 |
| Propylene Glycol | 0.25 | 1.00 | 0.50 | 0.50 | 1.00 | 0.25 |
| Ammonium Hydroxide | 0.30 | 0.00 | 0.00 | 0.00 | 0.00 | 0.00 |
| Isopropanol | 3.50 | 1.90 | 1.90 | 1.90 | 1.90 | 3.50 |
| Caustic Soda, 50% | 0.06 | 0.00 | 0.06 | 0.06 | 0.06 | 0.00 |
| Firmenich Fragrance | | 0.05 | 0.05 | 0.05 | 0.05 | |
| Measure pH | 11.7 | NA | NA | NA | NA | 3.96 |
| Fragrance to be added | 0.05 | OMIT | OMIT | OMIT | OMIT | OMIT |
| | 100.00 | 100.00 | 100.00 | 100.00 | 100.00 | 100.00 |

The results of the residue testing, using the gloss readings as taught above, are as follows;

| Example: | Change in Gloss: |
|---|---|
| Example 2C | 1.50 |
| Example 2G | 2.80 |
| Example 2F | 3.00 |
| Example 2E | 4.34 |
| Example 2D | 4.48 |
| Example 2 | 8.66 |
| No Treatment | 31.48 |
| Example 2A | 31.78 |
| Example 2B | 33.83 |

As can be seen, as compared to tile surfaces which received "No treatment", the formulae of this invention (Examples 2, and 2C–2G) showed significantly lower values for the change in gloss, indicating that less residue was left behind. On the other hand, the competitive examples (Examples 2A and 2B) showed no difference in change of gloss from the untreated tile samples.

Preferably, the consumer should begin with a clean shower surface before beginning to use the shower rinsing compositions of the present invention, as the rinsing composition is not a shower cleaner as traditionally utilized, but is a daily maintenance system for keeping showers clean and sanitary with a minimum of consumer effort. However, if the consumer begins treating soiled shower surfaces with the rinsing composition, the results will not likely be apparent for about 2 to 4 weeks, assuming that the product is used daily as instructed.

It is believed that the rinsing composition is best sprayed onto the shower surfaces with a conventional trigger sprayer or pressurized dispenser, or through shower head metering, preferably before any undesirable deposits dry and set. In subsequent showers, the water and mist from showering enhances the removal of deposits. Thus, the repeated cycles of spray application of shower rinsing composition, drying of shower surfaces, and subsequent showering serve to convey deposits via gravity (with the rinsing composition as the carrier) down to the shower drain.

Water rinsing other than the showering itself can be done, but is unnecessary. No wiping, scrubbing, or other mechanical action is necessary, in contrast to conventional cleaning agents which are used to remove deposits only after such deposits have dried. However, wiping may enhance the performance of the rinsing composition.

Furthermore, in contrast to simply rinsing the shower surfaces with plain tap water which typically leaves deposits, the rinsing composition of the present invention air-dries spot free with reduced visible streaking. The rinsing composition is also effective in maintaining bathtub surfaces and metallic bathroom fixtures substantially free of deposits.

EXAMPLE 3

A disinfecting composition according to the present invention was prepared according to the following formula:

| | |
|---|---|
| Sodium dodecyl benzene sulfonate | 0.2000 |
| Isopropanol, anhydrous | 3.5000 |
| Ethylene glycol n-hexyl ether | 0.9000 |
| Ethylene glycol n-butyl ether | 1.0000 |
| Ammonium Hydroxide | 0.3000 |
| Propylene glycol | 0.2500 |
| Fluorad ® FC-129 fluoro surfactant | 0.0200 |
| Caustic soda, 50% active | 0.0600 |
| Soft Water | balance |

Bacteria Testing

Example 3 was tested by the AOAC Germicidal Spray Test and determined to be efficacious against the following test systems at a 10 minute contact (exposure) time:

*Staphylococcus aureus*/ATCC 6538
*Salmonella choleraesuis*/ATCC 10708
*Pseudomonas aeruginosa*/ATCC 15442
*Escherichia coli*/ATCC 43890
*Enterococcus (Streptococcus) faecalis*/ATCC 19433
*Listeria monocytogenes*/ATCC 15313
*Pastuerella multocida*/ATCC 43137
*Shigella dysenteriae*/ATCC 29026
*Shigella flexneri*/ATCC 25875
*Shigella sonnei*/ATCC 25931
*Yersinia enterocolitica*/ATCC 9610
*Enteroccocus (Streptococcus) faecalis*/ATCC 51299
*Campylobacter fetus*/ATCC 27374

Virus (Disinfecting) Testing

Example 3 is efficacious against the following viruses at a 10 minute contact (exposure) time when tested by the ASTM E1053-91 test method:

Herpes simplex virus type 1

Herpes simplex virus type 2

Influenza virus type A2

Human Immunodeficiency Virus Type 1 (HIV)

Mold Test

The composition of Example 3 was tested against *Aspergillus Niger* ATCC 6275 by the EPA Hard Surface Mildew-Fungistatic Test and found to control or inhibit the growth of mold and mildew on hard surfaces.

Sanitizer Test

The composition of Example 3 was also tested by the "Sanitizer for Inanimate, Non-Food Contact Surfaces" test method prepared by the Registration Division, Office of Pesticide Programs, EPA, 1976. (DIS/TSS Guideline 10 dated Jan 7, 1982.) The composition of Example 3 was found to be efficacious as a non-food contact sanitizer at a one minute contact (exposure) time.

EXAMPLE 4

A series of 57 additional compositions in accordance with the present invention were prepared and tested for antibacterial effect, in accordance with the AOAC Germicidal Spray Test, at a 10 minute contact time. Unless indicated otherwise, the samples contained 0.9% Hexyl and 1.0% Butyl. The results of these tests are set forth in the Tables which follow. Abbreviations used in these tables are as follows:

butyl or but . . . ethylene glycol mono-butyl ether
hexyl or hex . . . ethylene glycol n-hexyl ether
pg . . . propylene glycol
IPA . . . isopropyl alcohol
PnB . . . propylene glycol n-butyl ether
PtB . . . propylene glycol t-butyl ether The AOAC (Association of Official Analytical Chemists) Germicidal Spray Test, 15th Edition 1990, section 961.02, was used to screen various formulations using 10 carriers per composition. The formulations were tested at a ten minute contact time against *Staphylococcus aureus* ATCC 6538. If 0, 1, 2, or 3 failures per ten carriers were obtained, the compositions were considered to be effective. Four or five failures per ten carriers indicated borderline efficacy when tested. Six to ten failures indicated a product was not effective.

Samples in which Hexyl was present in concentrations above 0.6% were effective, in the presence of Butyl. While the presence of Butyl appeared to increase the efficacy of other ethers to which it was added, inconsistent results were obtained when PnB and PtB were utilized. These glycols exhibited antibacterial properties only in the presence of Hexyl, up to concentrations of 5% of PnB. While it is not fully understood at this time, it has been found that when Hexyl is employed as the glycol ether component, it is necessary to have at least 0.01% Butyl present, and further, efficacy of the Hexyl does not become pronounced until the concentration of Hexyl exceeds 0.6% regardless of the concentration of Butyl with it. Conversely, the effectiveness of Butyl appears to be as an adjunct to another glycol ether, unless the concentration of Butyl exceeds 5%.

TABLE 2

Hexyl/Butyl Effects:

A

| Observations/Results: | no hexyl 126-2 | 0.10% hexyl 126-9 | 0.50% hexyl 126-14 | 0.60% hexyl 126-52 | 0.70% hexyl 126-53 | 0.80% hexyl 126-54 |
|---|---|---|---|---|---|---|
| pH | 11.59 | 11.59 | 11.54 | 11.42 | 11.39 | 11.38 |
| color | none | none | none | none | none | none |
| appearance | clear | clear | clear | clear | clear | clear |
| Micro results (# not passing) | 10 | 10 | 19 | 5 | 3 | 0 |
| # of plates/slides tested on | 10 | 10 | 20 | 10 | 10 | 10 |
| Micro retest(# not passing) | | | 10 | | | |
| # of plates/slides tested on | | | 10 | | | |

B

| Observations/Results: | no butyl 126-1 | 0.01% butyl 126-47 | 0.05% butyl 126-48 | 0.10% butyl 126-8 | 0.50% butyl 126-49 | 3.0% butyl 126-26 | 5.0% butyl 126-28 |
|---|---|---|---|---|---|---|---|
| pH | 11.60 | 11.39 | 11.47 | 11.58 | 11.38 | 11.54 | 11.52 |
| color | none | none | none | none | none | none | none |
| appearance | clear | clear | clear | clear | clear | clear | clear |
| Micro results (# not passing) | 9 | 0 | 0 | 5 | 0 | 1 | 1 |
| # of plates/slides tested on | 10 | 10 | 10 | 10 | 10 | 10 | 10 |
| Micro retest (# not passing) | 15 | | | 18 | | | |
| # of plates/slides tested on | 30 | | | 30 | | | |

C

| | no | 0% hex | .2% hex | .4% hex | .6% hex | .8% hex | 1% hex |
|---|---|---|---|---|---|---|---|

TABLE 2-continued

Hexyl/Butyl Effects:

| Observations/Results: | hex/but 126-41 | 5% but 126-51 | 1.7% but 126-42 | 1.5% but 126-43 | 1.3% but 126-44 | 1.1% but 126-45 | .9% but 126-46 |
|---|---|---|---|---|---|---|---|
| pH | 11.44 | 11.43 | 11.43 | 11.41 | 11.46 | 11.40 | 11.38 |
| color | none | none | none | none | none | none | none |
| appearance | clear | clear | clear | clear | clear | clear | clear |
| Micro results (# not passing) | 10 | 10 | 10 | 9 | 4 | 1 | 1 |
| # of plates/slides tested on | 10 | 10 | 10 | 10 | 10 | 10 | 10 |
| Micro retest (# not passing) | | | | | | | |
| # of plates/slides tested on | | | | | | | |

From the above, it may be seen that samples in which Hexyl was present in concentrations above 0.6% were effective, in the presence of at least 0.01% Butyl. While not fully understood, it appears that there is a synergism between the Hexyl and Butyl, since neither is effective without the other. Further, it is noted that when Hexyl and Butyl are used together, efficacy is not achieved until the Hexyl concentration is 0.6 or above.

TABLE 3

Propylene Glycol Effects:

| Observations/Results: | no pg 126-3 | 0.10% pg 126-12 | 1.0% pg 126-15 | 3.0% pg 126-27 | 5.0% pg 126-31 |
|---|---|---|---|---|---|
| pH | 11.59 | 11.59 | 11.57 | 11.57 | 11.55 |
| color | none | none | none | none | none |
| appearance | clear | clear | clear | clear | clear |
| Micro results (# not passing) | 1 | 3 | 3 | 1 | 2 |
| # of plates/slides tested on | 10 | 10 | 10 | 10 | 10 |
| Micro retest (# not passing) | 2 | | | | 3 |
| # of plates/slides tested on | 10 | | | | 10 |

From TABLE 3, above, one may conclude that the presence of propylene glycol is not critical to success of the present invention, but as previously indicated, its inclusion is beneficial for purposes of reduction of residue and streaking.

From TABLE 4, which follows, P-series glycol ethers are effective below 5%, when used in combination with Hexyl in a concentration above 0.6%. At concentrations of 5% or higher, the presence of Hexyl appears to be unnecessary in the case of propylene glycol n-butyl ether (PnB).

TABLE 4

P-Series Glycol Ether Effects:

| Observations/Results: | 2.0% PnB no hexyl 126-22 | 2.0% PnB no butyl 126-20 | 0.10% PnB, no hex/but 126-10 | 2.0% PnB, no hex/but 126-24 | 5.0% PnB, no hex/but 126-29 | 2.0% PTB no hexyl 126-23 | 2.0% PTB no butyl 126-21 | 0.10% PTB, no hex/but 126-11 | 2.0% PTB, no hex/but 126-25 | 0.05 PTB, no hex/but 126-30 |
|---|---|---|---|---|---|---|---|---|---|---|
| pH | 11.57 | 11.63 | 11.58 | 11.62 | 11.66 | 11.62 | 11.72 | 11.65 | 11.57 | 11.59 |
| color | none | white | none | none | none | none | none | none | none | none |
| appearance | clear | milky | clear | clear | clear | clear | clear | clear | clear | clear |
| Micro results (# not passing) | 10 | 0 | 10 | 10 | 1 | 10 | 1 | 10 | 9 | 10 |
| # of plates/slides tested on | 10 | 10 | 10 | 10 | 10 | 10 | 10 | 10 | 9 | 10 |
| Micro retest (# not passing) | | | | | 2 | | | | | |
| # of plates/slides tested on | | | | | 10 | | | | | |

TABLE 5

Primary Alcohol Effects:

A

| Observations/Results: | no IPA 126-4 | 1.0% IPA 126-16 | 2.00% IPA 126-55 | 5.0% IPA 126-32 | 10.0% IPA 126-36 |
|---|---|---|---|---|---|
| pH | 11.50 | 11.53 | 11.38 | 11.55 | 11.69 |
| color | none | none | none | none | none |
| appearance | clear | clear | clear | clear | clear |
| Micro results (# not passing) | 5 | 5 | 1 | 2 | 0 |
| # of plates/slides tested on | 10 | 10 | 10 | 10 | 10 |

TABLE 5-continued

Primary Alcohol Effects:

| | | | | | | | | | |
|---|---|---|---|---|---|---|---|---|---|
| Micro retest (# not passing) | 23 | | | | | | | | |
| # of plates/slides tested on | 30 | | | | | | | | |

| | B | | | | | | | | |
|---|---|---|---|---|---|---|---|---|---|
| Observations/Results: | 1.0% propanol no IPA 126-17 | 5.0% propanol no IPA 126-33 | 10.0% propanol no IPA 126-37 | 1.0% butanol no IPA 126-18 | 5.0% butanol no IPA 126-34 | 10.0% butanol no IPA 126-38 | 1.0% ethanol no IPA 126-19 | 5.0% ethanol no IPA 126-35 | 10.0% ethanol no IPA 126-39 |
| pH | 11.37 | 11.39 | 11.42 | 11.52 | 11.52 | 11.54 | 11.52 | 11.52 | 11.62 |
| color | none | none | none | none | white | white | none | none | none |
| appearance | clear | clear | clear | clear | milky | milky | clear | clear | clear |
| Micro results (# not passing) | 4 | 0 | 0 | 2 | 0 | 0 | 5 | 3 | 1 |
| # of plates/slides tested on | 10 | 10 | 10 | 10 | 10 | 9 | 10 | 10 | 10 |
| Micro retest (# not passing) | | | | | | | | | |
| # of plates/slides tested on | | | | | | | | | |

The presence of an aliphatic alcohol has been found to be beneficial, with the most benefit being obtained at concentrations above about 2% of isopropyl alcohol and above 5% for each of propanol, butanol, and ethanol.

compositions to a black glass surface, removing the composition by wiping with a cheesecloth wiper, allowing the glass to dry for 15 minutes, and then evaluating both visually and by reflectometer. It was found that by both measures, the

TABLE 6

Miscellaneous Effects:

| Observations/Results: | no Fluorad 126-5 | 0.01% Fluorad 126-7 | no NaOH 126-6 | 0.20% NaOH 126-13 | no NH3 1.03 g Citric 126-40A | no NH3 1.20 g Citric 126-40B | no NH3 1.06 g Citric 126-40C |
|---|---|---|---|---|---|---|---|
| pH | 11.56 | 11.59 | 10.47 | 12.19 | 8.98 | 8.05 | 7.04 |
| color | none | none | none | none | none | none | none |
| appearance | clear | clear | clear | clear | clear | clear | clear |
| Micro results (# not passing) | 3 | 2 | 1 | 1 | 1 | 3 | 0 |
| # of plates/slides tested on | 10 | 10 | 10 | 10 | 10 | 10 | 10 |
| Micro retest (# not passing) | 0 | | | | | | |
| # of plates/slides tested on | 10 | | | | | | |

| Observations/Results: | Example 2C | Example 2D | Example 2E | Example 2F | Example 2G |
|---|---|---|---|---|---|
| pH | NA | NA | NA | NA | 3.96 |
| color | none | none | none | none | none |
| appearance | clear | clear | clear | clear | clear |
| Micro results (# not passing) | 0 | 1 | 1 | 0 | 1 |
| # of plates/slides tested on | 10 | 10 | 10 | 10 | 10 |

| Observations/Results: | Example 2C | Example 2D | Example 2E | Example 2F | Example 2G |
|---|---|---|---|---|---|
| pH | NA | NA | NA | NA | 3.96 |
| color | none | none | none | none | none |
| appearance | clear | clear | clear | clear | clear |
| Micro results (# not passing) | 0 | 1 | 1 | 0 | 1 |
| # of plates/slides tested on | 10 | 10 | 10 | 10 | 10 |

The compositions of the present invention are equally effective for antibacterial activity both with and without the fluorosurfactant utilized. Efficacy is demonstrated at pH varying from about 4 to about 13.

Further to the above testing for antibacterial effect, the composition of Example 3 was compared with a commercially available competitive glass and surface cleaner and a commercially available competitive all purpose disinfectant. The comparison of streaking, or residue left on surface was conducted by applying a measured amount of each of the composition of Example 3 was significantly superior in terms of streaking and deposit of residue.

INDUSTRIAL APPLICABILITY

The compositions of the present invention are simple to produce and use. The compositions can be applied to surfaces to be disinfected in a variety of ways such as by sponging, spraying, mopping, wiping, foaming, dipping and in various other ways that are commonly used for conventional disinfecting and cleaning agents. The compositions may be also be dispensed from conventional pump, trigger or aerosol dispensers. The compositions may also be dispensed from sponges or towelettes which are pre-moistened with the compositions.

Thus the compositions of the present invention will find use as multipurpose disinfectants for many surfaces needing disinfection such as countertops, work areas, rest rooms, mirrors, shower doors and the like. The compositions can also be utilized to inhibit mold and mildew growth. Additionally, the compositions provide good detergency and streak-resistance on glass and polished surfaces.

Although the present invention has been illustrated with reference to certain preferred embodiments, it will be appreciated that the present invention is not limited to the specifics set forth therein. Those skilled in the art will readily appreciate numerous variations and modifications within the spirit and scope of the present invention, and all such variations and modifications are intended to be covered by the present invention.

What is claimed is:

1. A method for cleaning and sanitizing a non-porous hard surface in a household, commercial or institutional setting, said method comprising contacting said surface with a composition comprising from 1.0 to 5.0 percent by weight of an aliphatic alcohol, and from 0.9 to 8.0 percent by weight of a glycol ether, the composition being essentially free of conventional antibacterial agents including chlorine bleaches quaternary ammonium compounds and phenolic compounds.

2. A method as set forth in claim 1, wherein said composition further comprises a secondary alcohol selected from the group consisting of monohydric alcohols, dihydric alcohols, trihydric alcohols, and polyhydric alcohols.

3. A method as set forth in claim 2, wherein said secondary alcohol comprises propylene glycol.

4. A method for cleaning and sanitizing a surface, said method comprising contacting said surface with a composition comprising from 1.0 to 10.0 percent by weight of an aliphatic alcohol, and an organic ether, the composition being essentially free of chlorine bleaches, quaternary ammonium compounds and phenolic compounds, wherein said organic ether is selected from the group consisting of ethylene glycol n-hexyl ether, ethylene glycol mono-butyl ether, and mixtures thereof.

5. A method as set forth in claim 4, wherein said aliphatic alcohol comprises isopropanol.

6. A method as set forth in claim 5, wherein said composition further comprises a surfactant.

7. A method for sanitizing a surface, said method comprising contacting said surface with a composition comprising from 1.0 to 10.0 percent by weight of an aliphatic alcohol, and from 0.01 to 10.0 percent by weight of a glycol ether, the composition being essentially free of chlorine bleaches, quaternary ammonium compounds and phenolic compounds.

8. A method as set forth in claim 7, wherein said composition further comprises from 0.1 to 5.0 percent by weight of a secondary alcohol selected from the group consisting of monohydric alcohols, dihydric alcohols, trihydric alcohols, and polyhydric alcohols.

9. A method as set forth in claim 7, wherein said aliphatic alcohol is selected from the group consisting of isopropanol, propanol, butanol, and ethanol.

10. A method as set forth in claim 9, wherein said glycol ether is selected from the group consisting of ethylene glycol n-hexyl ether, ethylene glycol mono-butyl ether, and mixtures thereof.

11. A method as set forth in claim 9, wherein said glycol ether is a mixture of ethylene glycol n-hexyl ether and ethylene glycol mono-butyl ether, wherein said n-hexyl ether comprises from 0.6 to 1.0 percent by weight of said composition, and said mono-butyl ether comprises from 0.1 to 5.0 percent by weight of said composition.

12. A method as set forth in claim 11, wherein said n-hexyl ether comprises from 0.9 to 1.0 percent by weight of said composition.

13. A method as set forth in claim 12 wherein said aliphatic alcohol comprises isopropanol at a concentration of from 2 to 10 percent by weight of the composition.

14. A method as set forth in claim 12, wherein said aliphatic alcohol is selected from the group consisting of propanol, butanol, and ethanol, and said aliphatic, alcohol is present in a concentration of from 5 to 10 percent by weight of the composition.

15. A method according to claim 7 or claim 8, wherein said composition has a pH in the range of from about 7 to about 13.

16. A method for cleaning and sanitizing a shower surface, said method comprising contacting said shower surface with a composition consisting essentially of water, a surfactant, from 1.0 to 10 percent by weight of an aliphatic alcohol selected from the group consisting of isopropanol, propanol, butanol, and ethanol, from 0.9 to 1.0 percent by weight of ethylene glycol n-hexyl ether, from 1.0 to 5.0 percent by weight of ethylene glycol mono-butyl ether, and from 0.1 to 3.5 percent by weight of propylene glycol, said composition having a pH in the range of from about 7 to about 13.

17. A method as set forth in claim 16, wherein said composition further comprises a cleaning solvent, a thickener, fragrance, and a colorant, and said aliphatic alcohol is isopropanol.

18. A method for providing disinfection and mold and mildew inhibition to a shower surface, said method comprising contacting said shower surface with a composition consisting essentially of water, a surfactant, from 2.0 to 5.0 percent by weight of isopropanol, from 0.9 to 1.0 percent by weight of ethylene glycol n-hexyl ether, from 1.0 to 5.0 percent by weight of ethylene glycol mono-butyl ether, from 0.1 to 3.5 percent by weight of propylene glycol, a cleaning solvent, a thickener, fragrance, and a colorant, with said composition being at a pH in the range of from about 7 to about 13.

* * * * *